United States Patent [19]

Abraham et al.

[11] Patent Number: 5,993,844
[45] Date of Patent: Nov. 30, 1999

[54] CHEMICAL TREATMENT, WITHOUT DETERGENTS OR ENZYMES, OF TISSUE TO FORM AN ACELLULAR, COLLAGENOUS MATRIX

[75] Inventors: Ginger A. Abraham, Braintree; Robert M. Carr, Jr., West Roxbury, both of Mass.; Paul D. Kemp, Romiley, United Kingdom; Ryan Mercer, Boston; Linda Baker, Taunton, both of Mass.

[73] Assignee: Organogenesis, Inc., Canton, Mass.

[21] Appl. No.: 08/853,372

[22] Filed: May 8, 1997

[51] Int. Cl.⁶ .................. A61F 2/24; A61F 2/02; A01N 1/02
[52] U.S. Cl. .................. 424/423; 435/1.1; 424/422; 623/2; 623/11
[58] Field of Search .................. 424/422, 423; 623/2, 11; 435/1.1

[56] References Cited

U.S. PATENT DOCUMENTS

| | | |
|---|---|---|
| 3,329,572 | 7/1967 | Malgouzou .................. 167/74 |
| 3,551,560 | 12/1970 | Thiele .................. 424/95 |
| 5,007,934 | 4/1991 | Stone . | |
| 5,028,695 | 7/1991 | Eckmayer et al. .................. 530/356 |
| 5,263,984 | 11/1993 | Li et al. . | |
| 5,460,962 | 10/1995 | Kemp .................. 435/238 |
| 5,523,291 | 6/1996 | Janzen et al. .................. 514/21 |

FOREIGN PATENT DOCUMENTS

WO 9528183  10/1995  WIPO .

OTHER PUBLICATIONS

Courtman et al., J. of Biomedical Research, 28:655–666 (1994).
Wilson, G.J., et al., Ann. Thorac. Surg., 60:5353–5358 (1995).
Bodnar, E., et al., Thorac. Cardiovascular Surg., 34:82–85 (1986).

*Primary Examiner*—Sandra E. Saucier
*Attorney, Agent, or Firm*—Hale and Dorr LLP

[57] ABSTRACT

The invention is directed to collagenous tissues which have been treated to remove non-collagenous components such as cells, cellular debris, and other extracellular matrix components, such as proteoglycans and glycosaminoglycans, normally found in native tissues. Treatment of the tissue with alkali, chelating agents, acids and salts removes non-collagenous components from the collagenous tissue matrix while controlling the amount of swelling and dissolution so that the resultant collagen matrix retains its structural organization, integrity and bioremodelable properties. The process circumvents the need to use detergents and enzymes which detrimentally affect the cell compatibility, strength and bioremodelability of the collagen matrix. The collagenous tissue matrix is used for implantation, repair, or use in a mammalian host.

23 Claims, No Drawings

CHEMICAL TREATMENT, WITHOUT DETERGENTS OR ENZYMES, OF TISSUE TO FORM AN ACELLULAR, COLLAGENOUS MATRIX

BACKGROUND OF THE INVENTION

1. Field of the Invention

This invention is in the field of tissue engineering. The invention is directed to collagenous tissues which have been treated to remove non-collagenous components such as cells, cellular debris, and other extracellular matrix components, such as proteoglycans and glycosaminoglycans, normally found in native tissues. Treatment of the tissue with alkali, chelating agents, acids and salts removes non-collagenous components from the collagenous tissue matrix while controlling the amount of swelling and dissolution so that the resultant collagen matrix retains its structural organization, integrity and bioremodelable properties. The process circumvents the need to use detergents and enzymes which detrimentally affect the cell compatibility, strength and bioremodelability of the collagen matrix. The collagenous tissue matrix is used for implantation, repair, or use in a mammalian host.

2. Brief Description of the Background of the Invention

The field of tissue engineering combines the methods of the engineering with the principles of life sciences to understand the structural and functional relationships in normal and pathological mammalian tissues. The goal of tissue engineering is the development and ultimate application of biological substitutes to restore, maintain or improve tissue functions. [Skalak, R. and Fox, C. F., "Tissue Engineering", Alan R. Liss Inc. N.Y. (1988)]

Collagen is the principal structural protein in the body and constitutes approximately one-third of the total body protein. It comprises most of the organic matter of the skin, tendons, bones and teeth and occurs as fibrous inclusions in most other body structures. Some of the properties of collagen are its high tensile strength; its ion exchanging ability, due in part to the binding of electrolytes, metabolites and drugs; its low antigenicity, due to masking of potential antigenic determinants by the helical structure, and its low extensibility, semipermeability, and solubility. Furthermore collagen is a natural substance for cell adhesion. These properties and others make collagen a suitable material for tissue engineering and manufacture of implantable biological substitutes and bioremodelable prostheses.

As collagen is one major component of these biological substitutes, a method for obtaining sufficient quantities of collagen that is consistent in quality is needed. A need currently exists for an improved method for the removal of non-collagenous components such as cells, cellular debris, and other extracellular matrix components, such as proteoglycans and glycosaminoglycans, normally found in native tissues to yield a substantially pure native collagen matrix. Some of these non-collagenous structures that are present in native tissues are believed to be antigenic and will elicit a chronic inflammatory response when implanted in a host. However, in the art there are a variety of methods for the cleaning of such collagenous tissue which have resulted in collagenous compositions with different characteristics. The method used should be one that maintains the biological and physical properties of collagen and collagenous tissues suitable for use in tissue engineering.

In the art of treating a collagenous tissue to yield essentially a collagenous matrix, detergents and surfactants have customarily been used in the extraction of cells and lipids from the tissue. Detergents such as sodium dodecyl sulfate (SDS) are amphipathic molecules wherein the hydrophobic region binds to protein and are believed to increase the negative charge of the protein. When implanted, the increase in charge results in both the swelling of the tissue due to increased water binding by the hydrophilic region of the molecule, and decreased thermal stability in collagen by disrupting hydrogen bonding. Swelling both opens the structure of the collagen molecule making it susceptible to cellular enzymes such as collagenase and destabilizes the collagen matrix to result in a weakened construct. (Courtman, et al. Journal of Biomedical Materials Research 1994; 28:655–666.) It is further believed that SDS residues remain bound to the collagen and prevent cells from migrating into the implant. (Wilson, G J et al. Ann Thorac Surg 1995; 60:S353–8. Bodnar E, et al. "Damage of aortic valve tissue caused by the surfactant sodium dodecyl sulfate." Thorac Cardiovasc Surg 1986; 34:82–85.) Because detergents used in a chemical cleaning method can undesirably bind to and alter the bioremodeling capabilities of collagen in the treated tissue, the inventors have developed a method that eliminates the need for detergents.

Chemical cleaning of tissue with enzymes such as trypsin, pepsin and collagenase is known in the art but their use will result in chemical modification of the native collagen molecules and will adversely affect the structural integrity of the construct. Enzyme treatment of collagenous tissue is known in the art for removal and/or modification of extracellular matrix associated proteins. Proteases such as pepsin, trypsin, dispase, or thermolysin are used in the removal of collagen telopeptides to yield atelopeptide collagen. Collagen telopeptides are the non-triple helical portion of the collagen molecule and have been thought by some researchers to be weakly antigenic while by others they are thought to be responsible for the strong mechanical properties of collagen. Limited digestion of collagenous tissue will remove telopeptides without dissociation of the collagen matrix of the tissue, while prolonged digestion will dissociate the collagen fibrils into atelopeptide collagen monomers. It is also known in the art to modify and remove nucleic acids from the matrix using enzymes that digest endogenous RNA and DNA through use of RNAse and DNAse, respectively. As treatment with enzymes can affect the structural integrity of the collagen, the present method of the invention circumvents their use.

Methods for obtaining collagenous tissue and tissue structures from explanted mammalian tissue, and processes for constructing prostheses from the tissue, have been widely investigated for surgical repair or for tissue and organ replacement. The tissue is typically treated to remove potentially cytotoxic cellular and noncollagenous components to leave a natural tissue matrix. Further processing, such as crosslinking, disinfecting or forming into shapes have also been investigated. Previous methods for treating collagenous tissue to remove tissue components from the organized tissue matrix have employed detergents, enzymes or promote uncontrolled swelling of the matrix. WO 95/28183 to Jaffe, et al. discloses methods to decrease or prevent bioprosthetic heart valve mineralization postimplantation. The disclosed methods provide biological material made acellular by controlled autolysis. Autolysis is controllably performed using at least one buffer solution at a preselected pH to allow autolytic enzymes present in the tissue to degrade cellular structural components. U.S. Pat. No. 5,007,934 to Stone and, similarly, U.S. Pat. No. 5,263,984 to Li, et al. both disclose a multiple step method for chemical cleaning of ligamentous tissue. The method utilizes a detergent to remove lipids associated with cell membranes or collagenous tissue. U.S. Pat. No. 5,523,291 to Janzen, et al. discloses an comminuted injectable implant composition for soft tissue augmentation derived from ligamentum nuchae. The ligament is treated with a series soaks in a strongly alkaline solution of sodium hydroxide followed by hydrochloric acid solution and then sodium bicarbonate. U.S. Pat. No. 5,028,695 to Eckmayer, et al. discloses a process for the manufacture of collagen membranes in which collagenous tissue is repeatedly treated with a strong alkali and subsequently with a strong acid for a number of times then further treated with inorganic saline treatment to shrink the membranes and then with solvent to dry them.

SUMMARY OF THE INVENTION

Bioremodelable collagenous tissue matrices and methods for chemical cleaning of native tissue to produce such tissue matrices are disclosed.

The present invention overcomes the difficulties in obtaining bioremodelable tissue matrices that are substantially collagen. The invention provides tissue matrices that can be used as a prosthetic device or material for use in the repair, augmentation, or replacement of damaged and diseased tissues and organs.

The chemical cleaning method of this invention renders biological material, such as native tissues and tissue structures, substantially acellular and substantially free of non-collagenous components while maintaining the structural integrity of the collagenous tissue matrix. As detergents are not used in the chemical cleaning process, detergent residues that would normally remain bound to the tissue matrix are not present. As enzymes are not used, the collagen telopeptides are retained on the collagen molecules. The method comprises contacting a normally cellular native tissue with a chelating agent at a basic pH, contacting the tissue with salt solution at an acidic pH, contacting the tissue with a salt solution at a physiologic pH, and, then finally rinsing the resultant chemically cleaned tissue matrix.

This invention is directed to a chemically cleaned tissue matrix derived from native, normally cellular tissues. The cleaned tissue matrix is essentially collagen with intact rendered substantially free of glycoproteins, glycosaminoglycans, proteoglycans, lipids, non-collagenous proteins and nucleic acids such as DNA and RNA. Importantly, the bioremodelability of the tissue matrix is preserved as it is free of bound detergent residues that would adversely affect the bioremodelability of the collagen. Further the collagen is telopeptide collagen as the telopeptide regions of the collagen molecules remain intact as it has not undergone treatment or modification with enzymes during the cleaning process.

The collagenous material generally maintains the overall shape of the tissue it is derived from but it may be layered and bonded together to form multilayer sheets, tubes, or complex shaped prostheses. The bonded collagen layers of the invention are structurally stable, pliable, semipermeable, and suturable. When the matrix material is implanted into a mammalian host, undergoes biodegradation accompanied by adequate living cell replacement, or neo-tissue formation, such that the original implanted material is ultimately remodeled and replaced by host derived tissue and cells.

It is, therefore, an object of this invention to provide a method for cleaning native tissue resulting in a tissue matrix that does not exhibit many of the shortcomings associated with many of the methods developed previously. The method effectively removes non-collagenous components of native tissue without the use of detergents or enzymes to yield a tissue matrix comprised substantially of collagen.

Another object is the provision of a bioremodelable tissue matrix material that will allow for and facilitate tissue ingrowth and/or organ regeneration at the site of implantation. Prostheses prepared from this material, when engrafted to a recipient host or patient, concomitantly undergoes controlled bioremodeling and adequate living cell replacement such that the original implanted prosthesis is remodeled by the patient's living cells to form a regenerated organ or tissue.

Still another object of this invention is to provide a method for use of a novel multi-purpose bioremodelable matrix material in autografting, allografting, and heterografting indications.

Still a further object is to provide a novel tissue matrix material that can be implanted using conventional surgical techniques.

DETAILED DESCRIPTION OF THE INVENTION

The present invention provides a method for processing native collagenous tissues for transplantation. The processing method is designed to generate an implantable, graftable collagenous biological tissue material, an extracellular matrix comprising collagen, that serves as a scaffold that can be bioremodeled by a host in vivo or by living cells in culture in vitro.

This invention is further directed to a tissue engineered prostheses formed from processed native collagenous tissue, which, when implanted into a mammalian host, can serve as a functioning repair, augmentation, or replacement body part, or tissue structure, and will undergo controlled biodegradation occurring concomitantly with remodeling by the host's cells. The tissue matrix can be used as a prosthetic material for autografting, allografting, and heterografting indications. The prosthesis of this invention, in its various embodiments, thus has dual properties: First, it functions as a substitute body part, and second, while still functioning as a substitute body part, it functions as a remodeling template for the ingrowth of host cells. Although the prostheses will be illustrated through construction of various devices and constructs, the invention is not so limited. It will be appreciated that the device design in its material, shape and thickness is to be selected depending on the ultimate indication for the construct.

The chemical cleaning method of this invention renders biological material, such as native tissues and tissue structures, substantially acellular and substantially free of non-collagenous components while maintaining the structural integrity of the collagenous tissue matrix. Elastin is sometimes present in native tissue in small amounts and is not removed by the chemical cleaning method. The presence of elastin may be desirable for certain applications. As used herein, the term, "substantially acellular" means having at least 95% fewer native cells and cell structures than the natural state of the biological material. "Cells and cellular structures" refer to cells, living or not living, cell remnants, cell membranes and membrane structures. By use of the term, "substantially free of non-collagenous components", means that glycoproteins, glycosaminoglycans, proteoglycans, lipids, non-collagenous proteins and nucleic acids such as DNA and RNA comprise less than 5% of the resultant tissue matrix. As detergents are not used in the chemical cleaning process, detergent residues that would normally remain bound to the tissue matrix are not present. As enzymes are not used, the collagen telopeptides are retained on the collagen molecules. Further, the chemical cleaning method renders the biological material both sterile and endotoxin free when processed using sterile equipment, solutions and aseptic technique.

The term, "structural integrity", refers to the capacity of the chemically cleaned collagenous tissue matrix to withstand forces such as tension, compression, and support The structural integrity of the biological material is preserved as swelling is minimized in the chemical treatment steps even though some swelling will occur during treatment. Uncontrolled or excessive swelling both opens the structure of the collagen molecule making it susceptible to cellular enzymes such as collagenase and destabilizes the collagen to result in a weakened construct. As swelling affects the intramolecular structure of the collagen molecule, it affects the overall structure of the material on a intermolecular level by disrupting the native crosslinks between collagen molecules. Together, the structure of the collagen molecule and the crosslinks between collagen molecules lend structural integrity to the material.

Tissue matrix material that maintains much of its native structural integrity is useful, for instance, when used as a prosthetic device or as material to construct mulitilayered or complex devices. The integrity of the material is important if it is to perform a load bearing function such as a body wall support, a vascular device, or an orthopedic device. Related to structural integrity is the term "suturable" which means that the mechanical properties of the material includes suture retention which permits needles and suture materials to pass through the prosthesis material at the time of suturing of the prosthesis to sections of native tissue, a process known as anastomosis. During suturing, such prostheses must not tear as a result of the tensile forces applied to them by the suture, nor should they tear when the suture is knotted. Suturability of the prosthetic material, i.e., the ability of prostheses to resist tearing while being sutured, is related to the intrinsic mechanical strength of the prosthesis material, the thickness of the graft, the tension applied to the suture, and the rate at which the knot is pulled closed.

Biological material as defined in the invention includes but is not limited to harvested mammalian tissues, and structures thereof, derived from human, bovine, porcine, canine, ovine, caprine, and equine organisms. Tissue structures such as dermis, artery, vein, pericardium, heart valve, dura mater, ligament, intestine and fascia are all preferred tissue structures that are able to be cleaned by the methods of this invention to yield a tissue matrix that is substantially acellular and substantially free of non-collagenous components.

A preferred source of mammalian tissue is the tunica submucosa from small intestine, most preferably from porcine small intestine. In native small intestine, the tunic submucosa is the connective tissue layer of the organ and comprises both lymphatic and blood vessel cells. Methods for obtaining tunica submucosa are disclosed in WO 96/31157 and is incorporated herein. To obtain porcine tunica submucosa, also termed "submucosa", the small intestine of a pig is harvested and mechanically stripped, preferably by use of a gut cleaning machine (Bitterling, Nottingham, UK). The gut cleaning machine forcibly removes the fat, muscle and mucosal layers from the tunica submucosa using a combination of mechanical action and washing with water. The mechanical action can be described as a series of rollers that compress and strip away the successive layers from the tunica submucosa when the intact intestine is ran between them. As the tunica submucosa of the small intestine is comparatively harder and stiffer than the surrounding tissue, the softer components from the submucosa are removed from the tunica submucosa. The result of the machine cleaning is such that the mesenteric tissues, the tunica serosa and the tunica muscularis from the ablumen of the tunica submucosa and as well as the layers of the tunica mucosa from the lumen of the tunica submucosa are removed from the tunica submucosa so that the tunica submucosa layer of the intestine solely remains. The chemically cleaned tissue matrix of the tunica submucosa is also termed "intestinal collagen layer" or "ICL". It is noted that in some animal sources, such as carnivores and omnivores, the small intestine includes a stratum compactum which is also removed by this mechanical cleaning step.

Other methods of mechanically stripping layers of the small intestine are known in the art as described in U.S. Pat. No. 4,902,508 to Badylak, incorporated herein by reference. The method disclosed by this patent includes mild abrasion of the intestinal tissue to remove the abluminal layers, including the tunica serosa and the tunica muscularis, and the inner layers consisting of at least the luminal portion of the tunica mucosa. The layers that remain are the tunica submucosa with the attached basilar layer consisting of lamina muscularis mucosa and, if initially present in the harvested mammalian tissue, stratum compactum. Intestinal material obtained by either method can be implanted or first formed into body wall or vascular device by a number of methods including suturing, stapling. adhesive compositions, chemical bonding and thermal bonding.

Terms pertaining to certain operating parameters are defined for the entire specification and the examples for amounts, times and temperatures that can be varied without departing from the spirit and scope of the invention. As used herein, an "effective amount" refers to the volume and concentration of composition required to obtain the effect desired. A preferred effective amount for the chemical cleaning of tissue is a ratio of 100:1 v/v of solution to tissue but volumes more or less can be determined by the skilled artisan when considering the shape, bulk, thickness, density, and cellularity of the tissue to be cleaned. The time required for the chemical steps to be effective can be appreciated by those of skill in the art when considering the cellularity, matrix density, and thickness of the material to be cleaned. Larger, thicker, or denser materials will take longer for the solutions to penetrate and equilibrate in tissue. The temperatures for the environment and the solutions used in the present invention is preferably at ambient room temperature, about 25° C., but can be anywhere in the range of above the freezing temperatures of the solutions used to less than the denaturation temperature of the tissue material being treated. Temperatures between about 4° C. to about 45° C. are sufficient for the cleaning treatment to be effective. Agitation is meant to be mechanical shaking or mixing and is used to improve the penetration of the chemical compositions into the tissue and to reduce the time needed for chemical treatment to be effective. The term "buffered solution" refers to an aqueous solution containing at least one agent which preserves the hydrogen ion concentration or pH of the solution.

In the preferred method, harvested tissue may need to be cleaned manually, as by gross dissection, and/or mechanically cleaned of excess tissues such as fat and vasculature. Manual cleaning may be necessary for some tissues for handling manageability during processing or for most effective chemical treatment.

The tissue is first treated by contacting the tissue with an effective amount of chelating agent, preferably physiologically alkaline to controllably limit swelling of the tissue matrix. Chelating agents enhance removal of cells, cell debris and basement membrane structures from the matrix by reducing divalent cation concentration. Alkaline treatment dissociates glycoproteins and glycosaminoglycans from the collagenous tissue and saponifies lipids. Chelating agents known in the art which may be used include, but are not limited to, ethylenediaminetetraacetic acid (EDTA) and ethylenebis(oxyethylenitrilo)tetraacetic acid (EGTA). EDTA is a preferred chelating agent and may be made more alkaline by the addition of sodium hydroxide (NaOH), calcium hydroxide $Ca(OH)_2$, sodium carbonate or sodium peroxide. EDTA or EGTA concentration is preferably between about 1 to about 200 mM; more preferably between about 50 to about 150 mM; most preferably around about 100 mM. NaOH concentration is preferably between about 0.001 to about 1 M; more preferably between about 0.001 to about 0.10 M; most preferably about 0.01 M. Other alkaline or basic agents can be determined by one of skill in the art to bring the pH of the chelating solution within the effective basic pH range. The final pH of the basic chelating solution should be preferably between about 8 and about 12, but more preferably between about 11.1 to about 11.8. In the most preferred embodiment, the tissue is contacted with a solution of 100 mM EDTA/10 mM NaOH in water. The tissue is contacted preferably by immersion in the alkaline chelating agent while more effective treatment is obtained by agitation of the tissue and the solution together for a time for the treatment step to be effective.

The tissue is then contacted with an effective amount of acidic solution, preferably containing a salt. Acid treatment also plays a role in the removal of glycoproteins and glycosaminoglycans as well as in the removal of non-collagenous proteins and nucleic acids such as DNA and RNA. Salt treatment controls swelling of the collagenous tissue matrix during acid treatment and is involved with removal of some glycoproteins and proteoglycans from the collagenous matrix. Acid solutions known in the art may be used and may include but are not limited to hydrochloric acid (HCl), acetic acid ($CH_3COOH$) and sulfuric acid ($H_2SO_4$). A preferred acid is hydrochloric acid (HCl) at a concentration preferably between about 0.5 to about 2 M, more preferably between about 0.75 to about 1.25 M; most preferably around 1 M. The final pH of the acid/salt solution is preferably between about 0 to about 1, more preferably between about 0 and 0.75, and most preferably between about 0.1 to about 0.5. Hydrochloric acid and other strong acids are most effective for breaking up nucleic acid molecules while weaker acids are less effective. Salts that may be used are preferably inorganic salts and include but are not limited to chloride salts such as sodium chloride (NaCl), calcium chloride ($CaCl_2$), and potassium chloride (KCl) while other effective salts may be determined by one of skill in the art. Preferably chloride salts are used at a concentration preferably between about 0.1 to about 2 M; more preferably between about 0.75 to about 1.25 M; most preferably around 1 M. A preferred chloride salt for use in the method is sodium chloride (NaCl). In the most preferred embodiment, the tissue is contacted with 1 M HCl/1 M NaCl in water. The tissue is contacted preferably by immersion in the acid/salt solution while effective treatment is obtained by agitation of the tissue and the solution together for a time for the treatment step to be effective.

The tissue is then contacted with a effective amount of salt solution which is preferably buffered to about a physiological pH. The buffered salt solution neutralizes the material while reducing swelling. Salts that may be used are preferably inorganic salts and include but are not limited to chloride salts such as sodium chloride (NaCl), calcium chloride ($CaCl_2$), and potassium chloride (KCl); and nitrogenous salts such as ammonium sulfate ($NH_3SO_4$) while other effective salts may be determined by one of skill in the art. Preferably chloride salts are used at a concentration preferably between about 0.1 to about 2 M; more preferably between about 0.75 to about 1.25 M; most preferably about 1 M. A preferred chloride salt for use in the method is sodium chloride (NaCl). Buffering agents are known in the art and include but are not limited to phosphate and borate solutions while others can be determined by the skilled artisan for use in the method. One preferred method to buffer the salt solution is to add phosphate buffered saline (PBS) preferably wherein the phosphate is at a concentration from about 0.001 to about 0.02 M and a salt concentration from about 0.07 to about 0.3 M to the salt solution. A preferred pH for the solution is between about 5 to about 9, more preferably between about 7 to about 8, most preferably between about 7.4 to about 7.6. In the most preferred embodiment, the tissue is contacted with 1 M sodium chloride (NaCl)10 mM phosphate buffered saline (PBS) at a pH of between about 7.0 to about 7.6. The tissue is contacted preferably by immersion in the buffered salt solution while effective treatment is obtained by agitation of the tissue and the solution together for a time for the treatment step to be effective.

After chemical cleaning treatment, the tissue is then preferably rinsed free of chemical cleaning agents by contacting it with an effective amount of rinse agent Agents such as water, isotonic saline solutions and physiological pH buffered solutions can be used and are contacted with the tissue for a time sufficient to remove the cleaning agents. A preferred rinse solution is physiological pH buffered saline such as phosphate buffered saline (PBS). Other means for rinsing the tissue of chemical cleaning agents can be determined by one of skill in the art. The cleaning steps of contacting the tissue with an alkaline chelating agent and contacting the tissue with a acid solution containing salt may be performed in either order to achieve substantially the same cleaning effect. The solutions may not be combined and performed as a single step, however.

A preferred composition of the invention is a chemically cleaned tissue matrix derived from native, normally cellular tissues. The cleaned tissue matrix is essentially acellular telopeptide collagen, about 93% by weight, with less than about 5% glycoproteins, glycosaminoglycans, proteoglycans, lipids, non-collagenous proteins and nucleic acids such as DNA and RNA. Importantly, the bioremodelability of the tissue matrix is preserved as it is free of bound detergent residues that would adversely affect the bioremodelability of the collagen. Additionally, the collagen molecules have retained their telopeptide regions as the tissue has not undergone treatment with enzymes during the cleaning process.

Tissue matrices are derived from dermis, artery, vein, pericardium, heart valves, dura mater, ligaments, intestine and fascia. A most preferred composition is a chemically cleaned intestinal collagen layer derived from the small intestine. Suitable sources for small intestine are mammalian organisms such as human, cow, pig, sheep, dog, goat or horse while small intestine of pig is the preferred source. In one preferred embodiment, the collagen layer comprises the tunica submucosa derived from porcine small intestine. In another embodiment, the collagen layer comprises the tunica submucosa and the basilar layers of the small intestine. The basilar layers consist of lamina muscularis mucosa and, if present in the native tissue, the stratum compactum.

The most preferred composition of the invention is the intestinal collagen layer, cleaned by the chemical cleaning method of the invention, is essentially collagen, primarily Type I collagen, with less than about 5% glycoproteins, glycosaminoglycans, proteoglycans, lipids, non-collageneous proteins and nucleic acids such as DNA and RNA. The collagen layer is free of bound detergent residues that would adversely affect the bioremodelability of the collagen. The collagen layer is substantially free of cells and cellular debris, including endogenous nucleic acids such as DNA and RNA and lipids. Further, the intestinal collagen layer is both sterile and endotoxin free when processed using sterile equipment, solutions and aseptic technique.

Once the collagenous tissue matrix has been rendered substantially acellular and free of substantially noncollagenous extracellular matrix components, prostheses for implantation or engraftment may be manufactured therefrom. Collagen layers may be sutured or bonded together by use of any variety of techniques known in the art Methods for bonding the layers may employ adhesives such as thrombin, fibrin or synthetic materials such as cyanomethacrylates or chemical crosslinking agents. Other methods may employ heat generated by laser, light, or microwaves. Convection ovens and heated liquid baths may also be employed.

Thermal welding of the collagen layers is the preferred method for bonding together the collagen layers of the invention. Methods for thermal welding of collagen are described in WO 95/22301, WO 96131157 and U.S. Pat. No. 5,571,216, the teachings of which are incorporated herein by reference. The ICL is first cut longitudinally and flattened onto a solid, flat plate. One or more successive layers are then superimposed onto one another, preferably in alternating perpendicular orientation. A second solid flat plate is placed on top of the layers and the two plates are clamped tightly together. The complete apparatus, clamped plates and collagen layers, are then heated for a time and under conditions sufficient to effect the bonding of the collagen layers together. The amount of heat applied should be sufficiently high to allow the collagen to bond, but not so high as to cause the collagen to irreversibly denature. The time of the heating and bonding will depend upon the type of collagen material layer used, the moisture content and thickness of the material, and the applied heat. A typical range of heat is from about 50° C. to about 75° C., more typically 60∞C. to 65° C. and most typically 62∞C. A typical range of times will be from about 7 minutes to about 24 hours, typically about one hour. The degree of heat and the amount of time that the heat is applied can be readily ascertained through routine experimentation by varying the heat and time parameters. The bonding step may be accomplished in a conventional oven, although other apparatus or heat applications may be used including, but not limited to, a water bath, laser energy, or electrical heat conduction. Immediately following the heating and bonding, the collagen layers are cooled, in air or a water bath, at a range between room temperature at 20∞C. and 1∞C. Rapid cooling, termed quenching, is required to stop the heating action and to create an effective bond between the collagen layers. To accomplish this step, the collagen layers may be cooled, typically in a water bath, with a temperature preferably between about 1° C. to about 10° C., most preferably about 4° C. Although cooling temperatures below 1° C. may be used, care will need to be taken not to freeze the collagen layers, which may cause structural damage. In addition, temperatures above 10° C. may be used in quenching, but if the temperature of the quench is too high, then the rate of cooling may not be sufficient to fix the collagen layers to one another.

In the preferred embodiment, the collagenous material is crosslinked. Crosslinking imparts increased strength and structural integrity to the formed prosthetic construct while regulating the bioremodeling of the collagen by cells when the construct is implanted into a patient. Collagen crosslinking agents include glutaraldehyde, formaldehyde, carbodiimides, hexamethylene diisocyanate, bisimidates, glyoxal, adipyl chloride, dialdehyde starch, and certain polyepoxy compounds such as glycol diglycidyl ether, polyol polyglycidyl ether and dicarboxylic acid diglycidylester. Dehydrothermal, UV irradiation and/or sugar-mediated methods may also be used. Collagen will also naturally crosslink with age standing at room temperature. However, crosslinking agents need not be limited to these examples as other crosslinking agents and methods known to those skilled in the art may be used. Crosslinking agents should be selected so as to produce a biocompatible material capable of being remodeled by host cells. A preferred crosslinking agent is 1-ethyl-3-(3-dimethylaminopropyl) carbodiimide hydrochloride (EDC). The crosslinking solution containing EDC and water may also contain acetone. Crosslinking with EDC had been described in International PCT Publication Nos. WO 95/22301 and WO 96/31157.

In some embodiments, additional collagenous layers may be added to either the outer or inner surfaces of the bonded collagen layers, either before or after crosslinking. In tubular constructs, as in a vascular construct, dense fibrillar collagen may be added to the luminal surface to create a smooth flow surface for its ultimate application as described in International PCT Publication No. WO 95/22301, incorporated herein by reference. This smooth collagenous layer also promotes host cell attachment, as in the formation of neointima, which facilitates ingrowth and bioremodeling of the construct. As described in International PCT Publication No. WO 95/22301, this smooth collagenous layer may be made from acid-extracted fibrillar or non-fibrillar collagen, which is predominantly type I collagen, but may also include other types of collagen. The collagen used may be derived from any number of mammalian sources, typically bovine, porcine, or ovine skin or tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen from bovine tendon are described, for example, in U.S. Pat. No. 5,106,949, incorporated herein by reference.

Heparin can be applied to the prosthesis, by a variety of well-known techniques. For illustration, heparin can be applied to the prosthesis in the following three ways. First, benzalkonium heparin (BA-Hep) solution can be applied to the prosthesis by dipping the prosthesis in the solution and then air-drying it. This procedure treats the collagen with an ionically bound BA-Hep complex. Second, EDC can be used to activate the heparin, then to covalently bond the heparin to the collagen fiber. Third, EDC can be used to activate the collagen, then covalently bond protamine to the collagen and then ionically bond heparin to the protamine. Many other coating, bonding, and attachment procedures are well known in the art which could also be used.

Treatment of the tissue matrix material with agents such as growth factors or pharmaceuticals in addition to or in substitution for heparin may be accomplished. The agents may include for example, growth factors to promote vascularization and epithelialization, such as macrophage derived growth factor (MDGF), platelet derived growth factor (PDGF), vascular endothelial cell derived growth factor (VEGF); antibiotics to fight any potential infection from the surgery implant; or nerve growth factors incorporated into the inner collagenous layer when the prosthesis is used as a conduit for nerve regeneration. In addition to or in substitution for drugs, matrix components such as proteoglycans or glycoproteins or glycosaminoglycans may be included within the construct.

The collagenous prosthesis thus formed can also be sterilized in a dilute peracetic acid solution with a neutral pH. Methods for sterilizing collagen are described U.S. Pat. No. 5,460,962 and are incorporated by reference herein. In the preferred method, the collagen is disinfected with a dilute peracetic acid solution at a neutral pH. The peracetic acid concentration is preferably between about 0.01 and 0.3% v/v in water at a neutralized pH between about pH 6 and pH 8. Alternatively, sterilization with gamma irradiation, at typically 2.5 Mrad, or with gas plasma can also be used to sterilize the collagen. Other methods known in the art for sterilizing collagen may also be used.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Chemical cleaning of mechanically stripped porcine small intestine

The small intestine of a pig was harvested and mechanically stripped, using a Bitterling gut cleaning machine (Nottingham, UK) which forcibly removes the fat, muscle and mucosal layers from the tunica submucosa using a combination of mechanical action and washing using water. The mechanical action can be described as a series of rollers that compress and strip away the successive layers from the tunica submucosa when the intact intestine is run between them. The tunica submucosa of the small intestine is comparatively harder and stiffer than the surrounding tissue, and the rollers squeeze the softer components from the submucosa. The result of the machine cleaning was such that the submucosal layer of the intestine solely remained. The remainder of the procedure was performed under aseptic conditions and at room temperature. The chemical solutions were all used at room temperature. The intestine was then cut lengthwise down the lumen and then cut into 15 cm sections. Material was weighed and placed into containers at a ratio of about 100:1 v/v of solution to intestinal material.

A. To each container containing intestine was added approximately 1 L solution of 0.22 mm (micron) filter sterilized 100 mM ethylenediaminetetraacetic tetrasodium salt (EDTA)/10 mM sodium hydroxide (NaOH) solution. Containers were then placed on a shaker table for about 18 hours at about 200 rpm. After shaking, the EDTA/NaOH solution was removed from each bottle.

B. To each container was then added approximately 1 L solution of 0.22 mm filter sterilized 1 M hydrochloric acid (HCl)/1 M sodium chloride (NaCl) solution. Containers were then placed on a shaker table for between about 6 to 8 hours at about 200 rpm. After shaking, the HCl/NaCl solution was removed from each container.

C. To each container was then added approximately 1 L solution of 0.22 mm filter sterilized 1 M sodium chloride (NaCl)/10 mM phosphate buffered saline (PBS). Containers were then placed on a shaker table for approximately 18 hours at 200 rpm. After shaking, the NaCl/PBS solution was removed from each container.

D. To each container was then added approximately 1 L solution of 0.22 mm filter sterilized 10 mM PBS. Containers were then placed on a shaker table for about two hours at 200 rpm. After shaking, the phosphate buffered saline was then removed from each container.

E. Finally, to each container was then added approximately 1 L of 0.22 mm filter sterilized water. Containers were then placed on a shaker table for about one hour at 200 rpm. After shaking, the water was then removed from each container.

Treated samples were cut and fixed for histological analyses. Hemotoxylin and eosin (H&E) and Masson trichrome staining was performed on both cross-section and long-section samples of both control and treated tissues. Treated tissue samples appeared free of cells and cellular debris while control samples appeared normally and expectedly very cellular.

Example 2

Chemical Cleaning of Porcine Heart Valve

A porcine heart was procured from a 1 pound piglet and shipped in physiological pH saline on ice. Within 4 hours, the heart valves were removed from the heart mass using scalpel and forceps. Some further gross dissection was performed to remove excess tissue from around the valves. One valve was retained as a control with sample pieces cut and fixed for various histological analyses while the other valve underwent the chemical cleaning process. The remainder of the procedure was performed under aseptic conditions and at room temperature. The chemical solutions were all used at room temperature.

The valve was placed into 1 L solution of 100 mM EDTA/10 mM NaOH for about 18 hours while agitating on a shaker platform. The valve was then placed into 1 L of 1 M HCl/1 M NaCl and agitated for 8 hours. The valve was then placed into 1 L solution of 1 M HCl/10 mM phosphate buffered saline (PBS) and agitated for about 18 hours. The valve was then rinsed in PBS for between about 2–4 hours and then finally rinsed in sterile water for about 1 hour while agitating. Treated sample pieces were then cut and fixed for various histological analyses.

Hemotoxylin and eosin (H&E) and Masson trichrome staining was performed on both cross-section and long-section samples of both control and treated valves. Treated valve samples appeared free of cells and cellular debris while control samples appeared normally and expectedly very cellular.

Example 3

Chemical Cleaning of Porcine Artery, Pericardium and Fascia

A segment of femoral artery, the entire pericardium, and fascia were procured from a 450 lb. sow. The tissues were shipped in physiological pH saline on ice. The tissues were dissected further to remove excess tissue. Samples of each tissue were taken without cleaning for control samples and fixed for various histological analyses while the remainder of the tissues underwent the chemical cleaning process. The remainder of the procedure was performed under aseptic conditions and at room temperature. The chemical solutions were all used at room temperature.

The tissues were separately placed into 1 L solution of 100 mM EDTA/10 mM and agitated on a shaker platform for about 18 hours. The tissues were then each separately placed into 1 L solution of 1 M HCl/1 M NaCl and agitated for 8 hours. Next, the tissues were separately placed into a 1 L solution of 1 M HCl/10 mM phosphate buffered saline (PBS) and then agitated for about 18 hours. The tissues were then separately rinsed in PBS for between about 2 to 4 hours and then finally rinsed in sterile water for about 1 hour while agitating. Treated sample pieces were then cut and fixed for various histological analyses.

Hemotoxylin and eosin (H&E) and Masson trichrome staining was performed on both cross-section and long-section samples of both control and treated tissues. Treated tissue samples appeared free of cells and cellular debris while control samples appeared normally and expectedly very cellular.

Example 4

Differently Ordered Chemical Cleaning

This procedure was performed under aseptic conditions and at room temperature and all chemical solutions were used at room temperature.

Mechanically stripped porcine intestine was cut into five 15 cm sections as described in example 1.

To each container was then added approximately 1 L of 0.22 mm filter sterilized solution of 1 M hydrochloric acid (HCl)/1 M sodium chloride (NaCl). Containers were then placed on a shaker table for between about 6 to 8 hours at about 200 rpm. After shaking, the HCl/NaCl solution was removed from each container.

To each container containing intestine was added approximately 1 L of 0.22 mm (micron) filter sterilized solution of 100 mM ethylenediaminetetraacetic (EDTA)/10 mM sodium hydroxide (NaOH) solution. Containers were then placed on a shaker table for about 18 hours at about 200 rpm. After shaking, the EDTA/NaOH solution was removed from each bottle.

To each container was then added approximately 1 L of 0.22 mm filter sterilized solution of 1 M sodium chloride (NaCl)/10 mM phosphate buffered saline (PBS). Containers were then placed on a shaker table for approximately 18 hours at 200 rpm. After shaking, NaCl/PBS solution was removed from each container.

To each container was then added approximately 1 L of 0.22 mm filter sterilized solution of 10 mM PBS. Containers were then placed on a shaker table for about one hour at 200 rpm. After shaking, the phosphate buffered saline was then removed from each container.

Finally, to each container was then added approximately 1 L of 0.22 mm filter sterilized water. Containers were then placed on a shaker table for about one hour at 200 rpm. After shaking, the water was then removed from each container.

Treated sample pieces were then cut and fixed for various histological analyses. Hemotoxylin and eosin (H&E) and Masson trichrome staining was performed on both cross-section and long-section samples of both control and treated tissues. Treated tissue samples appeared free of cells and cellular debris while control samples appeared normally and expectedly very cellular.

Example 5

Various alkaline and chelating agents

The cleaning of mechanically stripped porcine intestinal submucosa was followed as according to example 1. This procedure was performed under aseptic conditions and at room temperature and all chemical solutions were used at room temperature. The chemical cleaning process of example 1 was followed but with the substitution of the alkaline chelating agent of step A was substituted for other alkaline chelating agents of similar nature:

A. To each container containing intestine was added approximately 1 L of 0.22 mm (micron) filter sterilized solution of either 100 mM ethylenebis(oxyethylenitrilo) tetraacetic acid (EGTA)/10 mM NaOH; 100 mM EDTA/10 mM Ca(OH)2 (calcium hydroxide); or, 100 mM EDTA/10 mM K2CO3 (potassium carbonate) solution. Containers were then placed on a shaker table for about 18 hours at about 200 rpm. After shaking, the alkaline chelating agents solution was removed from each bottle.

B. To each container was then added approximately 1 L of 0.22 mm filter sterilized solution of 1 M hydrochloric acid (HCl)/1 M sodium chloride (NaCl) solution. Containers were then placed on a shaker table for between about 6 to 8 hours at about 200 rpm. After shaking, the HCl/NaCl solution was removed from each container.

C. To each container was then added approximately 1 L of 0.22 mm filter sterilized solution of 1 M sodium chloride (NaCl)/10 mM phosphate buffered saline (PBS). Containers were then placed on a shaker table for approximately 18 hours at 200 rpm. After shaking, NaCl/PBS solution was removed from each container.

D. To each container was then added approximately 1 of 0.22 mm filter sterilized solution of 10 mM PBS. Containers were then placed on a shaker table for about one hour at 200 rpm. After shaking, the phosphate buffered saline was then removed from each container.

E. Finally, to each container was then added approximately 1 of 0.22 mm filter sterilized water. Containers were then placed on a shaker table for about one hour at 200 rpm. After shaking, the water was then removed from each container. Samples were fixed for histological analyses.

Hemotoxylin and eosin (H&E) and Masson trichrome staining was performed on both cross-section and long-section samples of both control and treated tissues. Treated tissue samples appeared free of cells and cellular debris while control samples appeared normally and expectedly very cellular.

Example 6

Various acid and salt agents

The mechanically stripped porcine intestinal submucosa of example 1 was chemically cleaned using a substituted acid agent or substituted salt agent in step B. This procedure was performed under aseptic conditions and at room temperature and all chemical solutions were used at room temperature.

A. To each container containing intestine was added approximately 1 L solution of 0.22 mm (micron) filter sterilized 100 mM ethylenediaminetetraacetic tetrasodium salt (EDTA)/10 mM sodium hydroxide (NaOH) solution. Containers were then placed on a shaker table for about 18 hours at about 200 rpm. After shaking, the EDTA/NaOH solution was removed from each bottle.

B. To each container was then added approximately 1 L of 0.22 mm filter sterilized solution of either 1 M CH3COOH (acetic acid)/1 M NaCl or 1 M H2SO4 (sulfuric acid)/1 M NaCl solution. Containers were then placed on a shaker table for between about 6 to 8 hours at about 200 rpm. After shaking, the solution was removed from each container.

C. To each container was then added approximately 1 L of 0.22 mm filter sterilized 1 M sodium chloride (NaCl)/10 mM phosphate buffered saline (PBS). Containers were then placed on a shaker table for approximately 18 hours at 200 rpm. After shaking, NaCl/PBS solution was removed from each container.

D. To each container was then added approximately 1 L of 0.22 mm filter sterilized 10 mM PBS. Containers were then placed on a shaker table for about one hour at 200 rpm. After shaking, the phosphate buffered saline was then removed from each container.

E. Finally, to each container was added approximately 1 L of 0.22 mm filter sterilized water. Containers were then placed on a shaker table for about one hour at 200 rpm. After shaking, the water was then removed from each container.

Treated sample pieces were then cut and fixed for various histological analyses. Hemotoxylin and eosin (H&E) and Masson trichrome staining was performed on both cross-section and long-section samples of both control and treated tissues. Treated tissue samples appeared free of cells and cellular debris while control samples appeared normally and expectedly very cellular.

Example 7

Glycosaminoglycan (GAG) Content of ICL Determined by Cellulose

Acetate Gel Electrophoresis and Alcian Blue Assay

To determine GAG content of ICL, cellulose acetate gel electrophoresis with subsequent alcian blue stain was performed on extracts of chemically cleaned ICL.

Samples of ICL underwent the chemical cleaning regimen outlined in Example 1, cut into 0.125 cm2 pieces and placed into eppendorf tubes. To digest the samples, 100 µl of papain (0.1 mg/ml papain in 0.1 M sodium phosphate, 0.1 M sodium chloride, 0.005 M EDTA, 0.9 mg/ml cysteine, pH 5.8) was added to each tube and allowed to incubate for about 18 hours at 60° C. Standard containing known amounts of GAG (heparin) were prepared in parallel. Dowex (0.4 g HCl form) and 3 ml water were then added. After spinning to remove the Dowex resin, 1 ml was removed and lyophilized. The samples were then rehydrated in 100 µl purified water and centrifuged for about 5 minutes.

Samples were separated on cellulose-acetate sheets using the method of Newton, et al. (1974). Cellulose-acetate sheets were soaked in 0.1 M lithium chloride/EDTA buffer (pH 5.8) and blotted gently. Samples (5 µl each) were applied to the sheets at the cathode end and electrophoresed for 30 minutes at 5 mA.

Following electrophoresis, the sheets were immersed immediately in an alcian blue stain solution (0.2% alcian blue 8GX, 0.05 M magnesium chloride, 0.025 M sodium acetate buffer (pH 5.8) in 50% ethylene alcohol) and placed on a shaker platform for about 30 minutes at room temperature. The sheets were then destained in at least three washes of destaining solution (0.05 M magnesium chloride, 0.025 M sodium acetate buffer (pH 5.8) in 50% ethylene alcohol) for a total of about 30 minutes on a shaker platform. No detectable GAG staining was observed for papain digested ICL while as little as 0.005 microgram heparin standard was detectable.

These results showed that the total amount of GAG remaining in chemically cleaned ICL is less than 1% (dry weight).

Example 8

Lipid Content of ICL Determined by Methylene Chloride Extraction

ICL was laid out flat on plastic plates and air dried for two hours. Once dried, ICL was cut into smaller pieces of about 1 cm2 of which 1.100 g were transferred to a soxhlet thimble.

To a Kontes brand round bottom flask 24/40 was added 90 ml methylene chloride. The soxhlet was assembled in the fume hood with the bottom of the flask in a heated water bath and ice cooled water running through the distiller.

Extraction was allowed to proceed for four hours after which the soxhlet was disassembled. The round bottom flask containing the solvent and extracted material was left in the heated water bath until methylene chloride was evaporated until there remained 5 ml. The methylene chloride was then transferred to a 11×13 glass culture tube and the remaining solvent was boiled off. To the tube was added 2 ml of methylene chloride and the tube was capped immediately and the tube placed in a −20° C. freezer.

The weight of the extracted material was then determined. The glass tube was placed in an ice bath. The weight of a Ludiag 1.12 ml aluminum weigh boat was tared on a microbalance (Spectrum Supermicro). 10 µl of resuspended extraction was added to the weigh boat and the solvent was boiled off by placing the weigh boat on a hot plate for 45 seconds. The weigh boat was allowed to cool for about 190 seconds and was placed on the microbalance. The procedure was then repeated for extract volumes of 20 µl and 30 µl.

Results indicate that the percentage of lipid is less than about 0.7% lipid by weight in dry chemically cleaned ICL. In contrast, non-chemically cleaned ICL contains a higher fraction of lipid; at least about 1.5% by weight in dry ICL that has not been chemically cleaned by the method of the invention.

Example 9

Amino Acid Analysis of ICL

Collagens are proteins characterized by their triple-helical regions which have a repeating triplet of amino acids glycine-X-Y, where X is frequently proline and Y is often hydroxyproline. Hydroxyproline is frequently used as an amino acid to identify and quantify collagens. Udenfriend, Science, 152:1335–1340 (1966).

To determine complete amino acid analysis of ICL, PICO-TAG HPLC was performed on mechanically cleaned (not chemically cleaned) porcine ICL and chemically cleaned ICL. Hydroxyproline content was measured for both materials and compared.

Sample pieces of ICL from each condition weighing about from 0.31 to about 0.36 g were dried further using a CEM AVC80 oven (CEM Corp.; Matthews, N.C.). Smaller samples were cut from these dried ICL pieces weighing about 9.5 to about 13.1 mg. Samples were placed into screw cap culture tubes and the samples were then hydrolyzed (n=3 for each condition) in 1% phenol in 6 M HCl at 110° C. for about 16 hours. ICL hydrolysates were then diluted in 0.1 M HCl to normalize the material concentrations to 1 mg/ml. To labeled glass tubes (6×55), 20 ml of hydrolysates and 8 ml of 1.25 mmol/ml L-norleucine as an internal standard. Samples were then frozen and lyophilized. Samples were then re-dried by adding 20 ml of 2:2:1 ethanol:water:triethylamine to the tubes, freezing and lyophilizing. Samples were then derivatized for 20 minutes at room temperature by adding 20 ml of reagent (7:1:1:1 ethanol:water:triethylamine:PITC) followed by freezing and lyophilizing. Samples were finally suspended in 200 ml PICO-TAG Sample Diluent and aliquoted to HPLC vials.

Amino acid standards were prepared in the following manner: 0.1 ml of amino acid standard (Product #: A-9531, Sigma) was added to 1.9 ml 0.1 M HCl. Five serial dilutions at 1:1 were made using 0.1 M HCl. Volumes of 100 ml for each serial dilution and 8 ml of 1.25 mmol/ml L-norleucine were together added to glass tubes (6×55) and then prepared in the same manner as ICL samples.

Samples and standards were run on a 3.9×150 mm PICO-TAG Amino Acid column (Part# 88131; Waters Corp.; Milford, Mass.). Injections of 10 ml for samples and 20 ml for standards were analyzed in triplicate for each.

Results indicate for chemically cleaned ICL material, the content of major collagenous amino acids in the material approach that of purified collagen preparations. Using the hydroxyproline as a measure of collagen content, the percentage of collagen by weight in ICL is calculated to be at least about 93% collagen by weight. In contrast, non-chemically cleaned ICL contains a high fraction of non-collagenous amino acids; between about 11 to 25% by weight of ICL is non-collagenous material.

Although the foregoing invention has been described in some detail by way of illustration and example for purposes of clarity and understanding, it will be obvious to one of skill in the art that certain changes and modifications may be practiced within the scope of the appended claims.

We claim:

1. A detergent-free and enzyme-free method for the removal of non-collagenous components from native mammalian tissue to yield an essentially collagenous tissue matrix that maintains its structural integrity, comprising:

(a) contacting the tissue with an alkaline solution containing a chelating agent selected from the group consisting of ethylenediaminetetraacetic acid and ethylenebis(oxyethylenitrilo)tetraacetic acid wherein the concentration of the chelating agent in the alkaline solution is between about 1 to about 200 mM and wherein the pH of the solution is between about 8 to about 12;

(b) contacting the tissue with an acidic solution containing a salt wherein the concentration of the salt in the acidic solution is between about 0.1 to about 2 M and wherein the pH of the solution is between 0 and about 1;

(c) contacting the tissue with a salt solution with a pH between about 5 and about 9; and, (d) contacting the tissue with a rinse agent, wherein the tissue maintains its structural integrity.

2. The method of claim 1 wherein the concentration of the chelating agent is between about 50 to about 150 mM.

3. The method of claim 1 wherein the alkaline solution of step (a) contains an alkali selected from the group consisting of sodium hydroxide, calcium hydroxide, sodium carbonate or sodium peroxide.

4. The method of claim 3 wherein the concentration of the alkaline agent is between about 0.001 to about 1 M.

5. The method of claim 1 wherein the acidic solution of step (b) is selected from the group consisting of hydrochloric acid, acetic acid and sulfuric acid.

6. The method of claim 5 wherein the concentration of the acid in the acidic solution is between about 0.5 to about 2 M.

7. The method of claim 5 wherein the concentration of the acid in the acidic solution between about 0.95 to about 1.25 M.

8. The method of claim 5 wherein the concentration of the acid in the acidic solution is around 1 M.

9. The method of claim 1 wherein the pH of the acid-salt solution is between 0 and 0.75.

10. The method of claim 1 wherein the pH of the acid-salt solution is between 0.1 to about 0.5.

11. The method of claim 1 wherein the salt of either of steps (b) or (c) is an inorganic salt.

12. The method of claim 1 wherein the salt of either of steps (b) or (c) is selected from the group consisting of sodium chloride, calcium chloride, potassium chloride and ammonium sulfate.

13. The method of claim 1 wherein the salt of either of steps (b) or (c) is at a concentration between about 0.1 to about 2 M.

14. The method of claim 1 wherein the salt of either of steps (b) or (c) is at a concentration 0.75 to about 1.25 M.

15. The method of claim 1 wherein the salt of either of steps (b) or (c) is at a concentration around 1 M.

16. The method of claim 1 wherein said tissue is selected from the group consisting of dermis, artery, vein, pericardium, heart valve, dura mater, ligament, bone, cartilage, fascia and intestine.

17. The method of claim 16 wherein said intestinal tissue comprises the tunica submucosa of the small intestine.

18. The method of claim 16 wherein said tissue is human, bovine, porcine, ovine, canine, caprine, or equine derived.

19. The method of claim 1 wherein the rinse agent is selected from the group consisting of water and a saline solution.

20. The method of claim 1 wherein step (b) is performed before step (a).

21. A detergent-free and enzyme-free method for the removal of non-collagenous components from native mammalian tissue to yield an essentially collagenous tissue matrix that maintains its structural integrity, comprising:

(a) contacting the tissue with a basic solution of ethylenediaminetetraacetic acid at a pH between about 8 and about 12;

(b) contacting the tissue with an acidic solution of sodium chloride at a pH between about 0 and about 1;

(c) contacting the tissue with a solution of sodium chloride at a pH between about 5 and about 9; and, (d) rinsing the tissue, wherein the tissue maintains its structural integrity.

22. A bioremodelable collagenous tissue matrix obtained by the method of claim 1 or 21.

23. A bioremodelable collagenous tissue matrix composition derived from native tissue selected from the group consisting of dermis, artery, vein, pericardium, heart valve, dura mater, ligament, bone, cartilage, fascia and intestine, wherein the collagenous tissue matrix is free of detergent residues, enzymatic modification and cells and cellular debris; and comprises telopeptide collagen;

elastin, wherein elastin is less than 10% of the total composition based on dry weight; and, non-collagenous and non-elastinous components wherein said components are less than 5% of the total composition based on dry weight.

* * * * *